United States Patent [19]
Nohira et al.

[11] Patent Number: 4,950,772
[45] Date of Patent: Aug. 21, 1990

[54] METHOD OF RACEMIZATION OF OPTICALLY ACTIVE TETRAHYDROFURAN-2-CARBOXYLIC ACID

[75] Inventors: Hiroyuki Nohira, Urawa; Shoko Takebayashi, Tokyo; Atsushi Yuzawa, Iwaki; Masami Yajima, Kitaibaraki, all of Japan

[73] Assignee: Yamakawa Chemical Industry Co., Ltd., Tokyo, Japan

[21] Appl. No.: 429,425

[22] Filed: Oct. 31, 1989

[30] Foreign Application Priority Data

Nov. 1, 1988 [JP] Japan .................................. 63-227129

[51] Int. Cl.$^5$ ............................................ C07D 307/24
[52] U.S. Cl. ..................................................... 549/484
[58] Field of Search ........................................ 549/484

[56] References Cited
PUBLICATIONS

Berlanger et al., Canadian J. Chem., vol. 61, (1983), 1383.

Primary Examiner—Richard L. Raymond
Attorney, Agent, or Firm—Varndell Legal Group

[57] ABSTRACT

Disclosed is a method of racemization of optically active tetrahydrofuran-2-carboxylic acid. (+)-Tetrahydrofuran-2-carboxylic acid is useful as a side chain intermediate of the antibiotics of penem series, and is prepared by optical resolution of racemic compound. The remaining (+)-isomer should be racemized and reused as the material for further optical resolution. The racemization can be, in accordance with the present invention, carried out by heating the optically active tetrahydrofuran-2-carboxylic acid to a temperature of 100° C. or higher in the presence of a strong base.

6 Claims, No Drawings

METHOD OF RACEMIZATION OF OPTICALLY ACTIVE TETRAHYDROFURAN-2-CARBOXYLIC ACID

BACKGROUND OF THE INVENTION

1. Field of the Invention

The present invention relates to a method of racemization of optically active tetrahydrofuran-2-carboxylic acid of the formula:

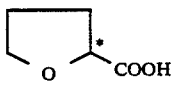

wherein the asterisk (*) indicates that the carbon atom with the mark is asymmetric.

2. State of the Art

There are two optically active isomers in tetrahydrofuran-2-carboxylic acid. Among them, (+)-isomer is useful as the sidechain intermediate for producing antibiotics of penem series, and obtained by optical resolution of tetrahydrofuran-2-carboxylic acid which is industrially produced as a racemate. The optical resolution of this compound was first achieved by Belanger et al (Can. J. Chem. 61, 1383 (1983)). The method, however, uses expensive brucine and ephedrine as the resolving agent.

It is advantageous to racemize the antipode remaining after one of the optically avtive isomers is separated by resolution, and to reuse the racemate in by further optical resolution. Therefore, it has been desired to establish the racemization technology. However, there has not been known an efficient way of racemizing optically active tetrahydrofuran-2-carboxylic acid. Among various carboxylic acids, some, e.g., amino acids can be racemized by heating in an alkaline medium. The method is, however, far from practical use, because of a very low rate of racemization when applied in tetrahydrofuran-2-carboxylic acid.

SUMMARY OF THE INVENTION

The object of the present invention is to break through the present status of the technology and provide an industrilly advantageous method for carrying out the racemization of optically active tetrahydrofuran-2-carboxylic acid.

The method according to the present invention achieving the above mentioned object of racemizing optically active tetrahydrofuan-2-carbocylic acid comprises heating the substance in the presence of a strong base to a temperature of 100° C. or higher.

DETAILED EXPLANATION OF THE PREFERRED EMBODIMENTS

As the strong base to be used in the present method, caustic alkali such as sodium hydroxide and potassium hydroxide, particularly, the former is useful. Among the salts of alkali metals weak alkalis such as carbonates and bicarbonates are not so effective. Alcoholates such as methoxides or ethoxides of sodium or potassium are effective, but it is necessary to use anhydrous organic solvents, and it is disadvantageous to use the alcoholates for industrial practice.

The amount of the strong base to be used is, in general, necessarily 1.5 equivalent or more, preferably, 2.0–2.5 equivalents based on the optically active tetrahydrofuran-2-carboxylic acid.

Reaction medium may be any of polar solvents, but water is the most convenient to use. It is, however, necessary to use pressurized conditions for carrying out the method at a high temperature at which the racemization proceeds rapidly. Thus, it is possible as an alternative way to practice the method with use of an organic solvent having a boiling point exceeding 100° C. such as ethylene glycol (b.p. 197.6° C.) and heat to a temperature lower than the boiling point thereof or to the boiling point (in the latter case, the reaction will be carried out under the reflux condition) so as to use the normal pressure. Even if lower alcohols such as methanol, ethanol or 2-propanol may exist in the solvent, the racemization reaction will not be disturbed.

In case where water is used as the medium, the concentration of the caustic alkali is chosen in the range of 10 to 70%, preferably, in the range of 30 to 60%.

The suitable reaction temperature is about 140° to 160° C. when it is aimed to raise the rate of racemization reaction to a practical level and when the limitations due to durable pressure of the reaction vessel is taken into account.

As the reaction mechanism of the racemization, it is considered that the base in the medium pulls out the hydrogen atom bonded to the asymmetric carbon atom of 2-position of tetrahydrofuran-2-carboxylic acid to form a carbanion, which racemizes when it recombines with a proton.

It is considered that the oxygen atom neighboring to the asymmetric carbon atom suppresses the pulling out of the hydrogen atom by the base. However, it was out of the expectation that, while amino acids and hydroxy acids having the structures similar to that of tetrahydrofuran-2-carboxylic acid may be relatively easily racemized with a weak base, tetrahydrofuran-2-carboxylic acid can be racemized only with a very strong base and at a high temperature.

Even in case where a caustic alkali is used as the strong base, it should be added to the medium at a concentration of 10% or higher as noted above. On the other hand, it is disadvantageous to use a high concentration of 70% or higher for the racemization. This is considered to be due to decrease of free water in the medium.

It is our discovery that, in accordance with the present invention which uses the above noted reaction conditions, the optically active tetrahydrofuran-2-carboxylic acid can be racemized under the simple procedures without altering it to a derivative. There occurs no undersirable side reaction such as decomposition. The materials used are less expensive and the reaction conditions are not so severe, and therefore, the reaction vessel may be that with ordiary corrosion resistance and pressure resistance. Thus, the costs for the racemization is low.

Usually, racemization reaction is practiced in combination with the operation of obtaining the optically active tetrahydrofuran-2-carboxylic acid by the optical resolution of the racemate, and therefore, the optically active compounds to be racemized are often in the form of salts with resolving agents. The present method can be of course carried out with the isolated tetrahydrofuran-2-carboxylic acid from the salt thereof as well as without isolation, or using the salt as it is. This is convenient for industrial practice.

The obtained racemic compound may be subjected to further optical resolution to obtain the optically active compound which is useful as the sidechain intermediate of the above mentioned antibiotics.

EXAMPLES

The following examples illustrate the present invention in detail.

In the examples, the racemization ratio is defined as follows:

Racemization ratio (%) = $(1 - [\alpha]/[\alpha]o) \times 100$ $[\alpha]$: specific rotation after the reaction
$[\alpha]o$: specific rotation before the reaction

Examples 1-4

Racemic tetrahydrofuran-2-carboxylic acid was subjected to the optical resolution to obtain (+)-isomer, and from the remaining mother liquor, tetrahydrofuran-2-carboxylic acid mainly consisting of (−)-isomer was recovered, which had $[\alpha]_D^{23} = -9.5°(c=1, CHCl_3)$. 10 Gramms of the acid (86.2 mmol) was used as the material and charged in a stainless steel reactor of the capacity 100 ml with 17.6 gramms of 49% sodium hydroxide (215.5 mmol of NaOH, molar ratio to the carboxylic acid is 2.5) and the reaction vessel was sealed and heated under the different conditions to cause the racemization reaction. After the reaction, 30 gramms of water was added to the reaction mixture. The mixture was acidified with hydrochloric acid, and then subjected to extration with methyl isobutyl ketone for a few times. The organic layer was collected for distilling off the solvent to obtain the racemized tetrahydrofuran-2-carboxylic acid.

The yields and the racemization ratios are shown below with the reaction conditions.

| No. | Temperature (°C.) | Period (hr) | Yield (%) | $[\alpha]_D^{23}$ (deg.) | Racemization Ratio (%) |
|---|---|---|---|---|---|
| 1 | 100 | 23 | 87 | −6.6 | 30.5 |
| 2 | 120 | 10 | 87 | −2.8 | 70.5 |
| 3 | 140 | 5 | 88 | 0 | 100 |
| 4 | 160 | 2 | 86 | 0 | 100 |

Example 5

10 Gramms of (−)-tetrahydrofuran-2-carboxylic acid, $[\alpha]_D^{23} -9.0°(c=1, CHCl_3)$ and 14.1 gramms of 49% sodium hydroxide water solution (172.7 mmol of NaOH, molar ratio 2.0) were taken in the reaction vessel. The same procedure as that of Examples 1-4 was repeated except for the reaction condition of 140° C. for 5 hrs.

Tetrahydrofuran-2-carboxylic acid of $[\alpha]_D^{23} -0.7°$ (c=1, CHCl_3) was obtained at the yield of 93%, and the racemization ratio was calculated to be 92%.

Example 6

The procedure of example 5 was repeated with the alteration 10.6 gramms (NaOH 129.9 mmol) of 49% sodium hydroxide was used so that the molar ratio of the alkali to the carboxylic acid may be 1.5.

Racemized tetrahydrofuran-2-carboxylic acid, $[\alpha]_D^{23} -3.3°$ (c=1, CHCl_3), was obtained at the yield of 95% and the racemization ratio of 63%.

Example 7

The procedure of example 5 was repeated with the alteration that 9.1 gramms of 95% sodium hydroxide (216.1 mmol) in the form of pellets was used as the strong base with 5.3 gramms of water.

The racemized tetrahydrofuran-2-carboxylic acid, $[\alpha]_D^{23} -0.8°$ (c=1, CHCl_3), was obtained at the yield of 86% and the racemization ratio of 91%.

Examples 8 and 9

The procedure of example 5 was repeated with the lowered concentration of aqueous sodium hydroxide as shown below.

The yields and the racemization ratio of the obtained tetrahydrofuran-2-carboxylic acid were as follows:

| No. | NaOH Concentration (%) | Product (g) | Yield (%) | $[\alpha]_D^{23}$ (deg.) | Racemization Ratio (%) |
|---|---|---|---|---|---|
| 8 | 30 (215.3 mmol) | 28.7 | 90 | −3.4 | 62 |
| 9 | 15 (215.6 mmol) | 57.5 | 89 | −6.2 | 31 |

Example 10

The racemization was tried with use of potassium hydroxide instead of sodium hydroxide. 24.7 Gramms of 49% water solution (KOH 216.1 mmol, molar ratio to the carboxylic acid 2.5) was used, and the procedure of example 3 was repeated.

Racemized tetrahydrofuran-2-caroxylic acid, $[\alpha]_D^{23} -0.7°$ (c=1, DHDl_3), was obtained at the yield of 74% and the racemization ratio of 92%.

We claim:

1. A method of racemization of optically active tetrahydrofuran-2-carboxylic acid, which comprises heating the optically active tetrahydrofuran-2-carboxylic acid in a reaction medium to a temperature of 100° C. or higher in the presence of a strong base.

2. A method of racemization according to claim 1, wherein sodium hydroxide or potassium hydroxide is used as the strong base, and the strong base is used in an amount of 1.5-2.5 equivalent to the optically active tetrahydrofuran-2-carboxylic acid, and at a concentration of 10-70 weight %, preferably, 30-60 weight %, in the reaction medium.

3. A method of racemization according to claim 1, wherein water is used as the reaction medium, and the reaction is carried out at a temperature of 140°-160° C.

4. A method of racemization according to claim 1, wherein an organic solvent having a boiling point exceeding 100° C. is used, and the reaction is carried out at a temperature of the boiling point or lower under normal pressure.

5. A method of racemization according to claim 2, wherein water is used as the reaction medium, and the reaction is carried out at a temperature of 140°-160° C.

6. A method of racemization according to claim 2, wherein an organic solvent having a boiling point exceeding 100° C., is used, and the reaction is carried out a temperature of the boiling point or lower under normal pressure.

* * * * *